Figure 1:
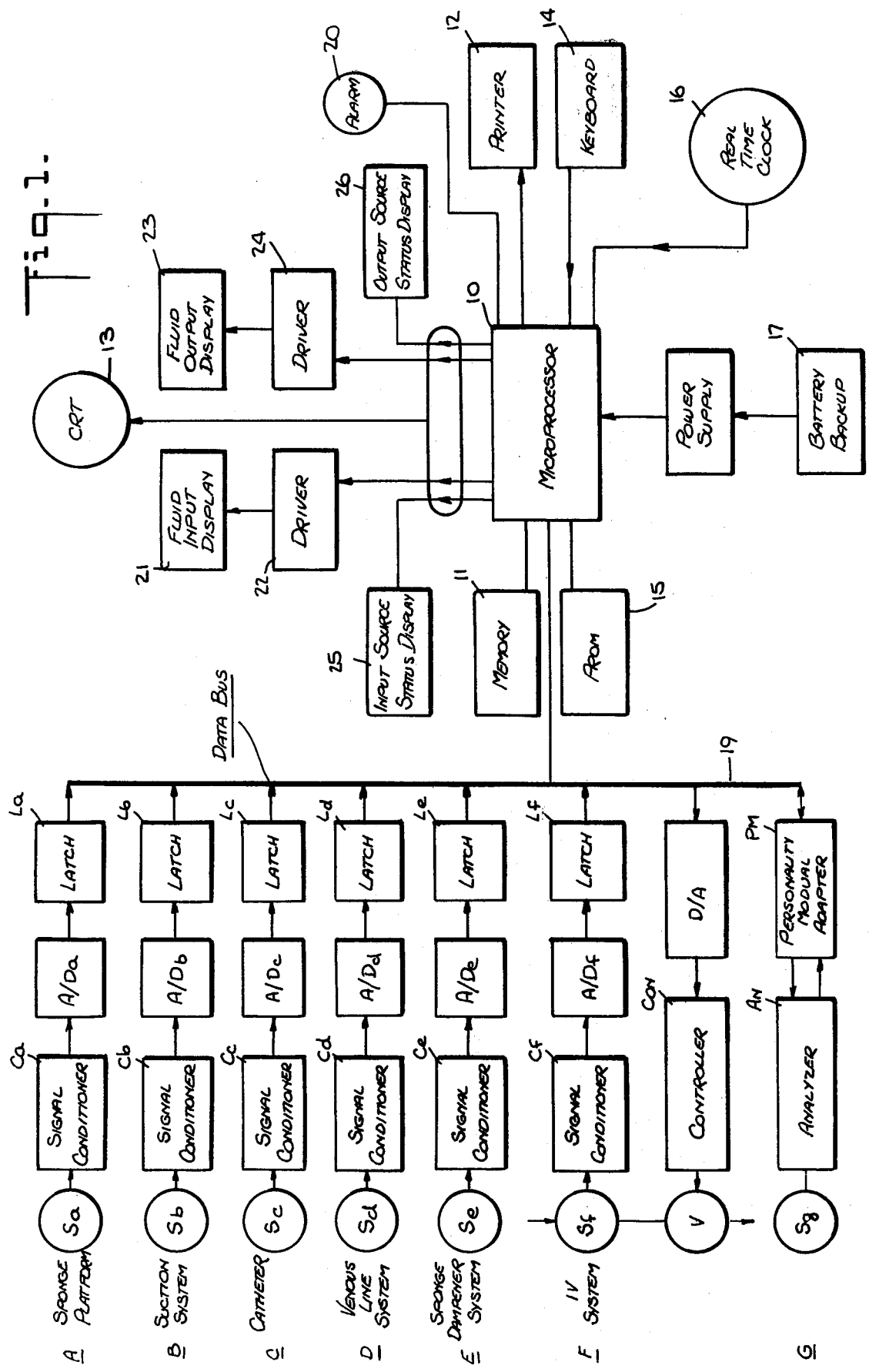

United States Patent [19]

Corbitt et al.

[11] 4,449,538

[45] May 22, 1984

[54] MEDICAL-ELECTRONIC BODY FLUID ACCOUNTING SYSTEM

[76] Inventors: John Corbitt, 1617 N. Fed. Hwy., Lake Worth, Fla. 33460; Thomas J. Michel, 1011 NW. 198th St., Miami, Fla. 33169

[21] Appl. No.: 342,365

[22] Filed: Jan. 25, 1982

[51] Int. Cl.³ .............................................. A61M 1/00
[52] U.S. Cl. .................................. 128/760; 128/762; 128/777; 364/415; 604/50; 604/65
[58] Field of Search ................. 73/195, 196; 364/415, 364/479, 500, 501, 502, 509, 510, 550; 604/31, 50, 65, 66, 67; 128/760, 762, 771

[56] References Cited

U.S. PATENT DOCUMENTS

| | | | |
|---|---|---|---|
| 4,146,029 | 3/1979 | Ellinwood | 128/260 |
| 4,216,462 | 8/1980 | McGroth et al. | 364/415 |
| 4,261,360 | 4/1981 | Perez | 128/DIG. 13 |

*Primary Examiner*—Kyle L. Howell
*Assistant Examiner*—George Yanulis
*Attorney, Agent, or Firm*—Michael Ebert

[57] ABSTRACT

A medical-electronic body fluid accounting system for use in surgical procedures and in post-operative and non-surgical care to afford a running account of the fluid intake to a patient and fluid outtake therefrom. The system is provided with a microcomputer to which is applied digital data derived from a plurality of fluid input source channels and fluid output source channels which together represent the prevailing fluid input and output sources associated with the patient. Included in the input source channels are those monitoring the flow of fluids being fed intraveneously into the patient, each such input channel having a sensor which generates a signal representing the volume of a particular fluid, such as a saline solution, being infused into the patient, this signal being converted into a corresponding digital value. Included in the output source channels is one having a sensor generating a signal representing the amount of fluid discharged through a urinary or other catheter, and another generating a signal representing the amount of exudate drawn from the surgical site, and still another to measure the amount of blood taken from the patient by sponges. On the basis of data acquired by the input and output channels, the computer yields a fluid intake total and a fluid outtake total, which totals are displayed to indicate the prevailing fluid balance.

16 Claims, 2 Drawing Figures

MEDICAL-ELECTRONIC BODY FLUID ACCOUNTING SYSTEM

BACKGROUND OF INVENTION

This invention relates generally to medical-electronic apparatus for monitoring the amount of fluid being administered to a patient and for concurrently metering the amount of fluid exhausted therefrom, and more particularly to a computerized body fluid accounting system for use in surgical procedures and in post-operative care which affords a running account of fluid intake and outtake.

In the course of a typical surgical procedure, intravenously (IV) administered to a patient are fluids whose properties are medically appropriate to the procedure. Among these are whole blood or plasma, Ringer's lactate, antibiotics and anti-coagulants as well as saline and dextrose solutions. The multiplicity of such fluid inputs imposes a difficult burden on the attending anesthesiologist or other specialist who, among his other responsibilities, must assess the volume of blood or other fluid which has been infused into the patient.

Since in modern practice, IV solutions are contained in collapsible plastic bags suspended at raised positions on stands, by observing the degree to which a particular bag has collapsed, one may, with a fair degree of accuracy, determine how much of a particular fluid has been delivered to the patient. But when an observer is called upon to monitor four or five hanging IV bags and at the same time to carry out other necessary tasks, his ability to make a reasonably accurate assessment of the fluid inputs may be impaired.

Moreover, it is not enough to assess the volume of fluid inputs to a patient, for proper patient care entails information regarding the prevailing fluid input-to-output balance. The observer must therefore also consider the volume of fluid being excreted or otherwise discharged from the patient through appropriate catheters by way of the urinary, anal or gastrointestinal tract. Also, one must take into account the loss of blood; for in the course of a surgical procedure, blood and other body fluids are extracted from the surgical site by suction pumps as well as by absorbent sponges.

Both the anesthesiologist and surgeons in a surgical procedure must monitor the amount of blood infused to and removed from a patient. Since the surgeon's mind is on one set of immediate tasks and the anesthesiologist's on another (only part of which is monitoring fluid flow), a disparity often arises between the surgeon's and the anesthesiologist's assessments as to how much blood has really been taken out of and put into a patient. In some cases this disagreement is responsible for the loss of the patient due to congestive heart failure, circulatory disfunction, or other volume-related difficulties. With present day high technology surgical methods, it is nearly impossible to keep count of so many variables when they are not centralized at a point where rapid analysis can be made. In a complex operation such as open heart surgery and other cases involving deep thorasic surgery, there may be a multiplicity of suction pumps as well as a multiplicity of surgeons working on a patient. This can occur in emergency conditions or during extremely complex operations; i.e., heart transplants and open heart surgery. In these situations, the automatic tallying of suction fluids is mandated by the fact that it is impossible to keep up with the traffic of fluid loss from a patient when there are several wound sites or surgical routes for fluids to leave the body. A single point integration of data available for reference then becomes imperative.

In the normal course of a surgical procedure with a multiplicity of bags present, it is not impossible for the anesthesiologist to assess precise amounts of fluid, but when there is a crisis in the operating room the full attention of the surgical staff including the anesthesiologist is then directed toward solving the immediate problem. It is during these periods, when fluid balance is at a very critical level and no one has time to pay attention to it, that fluid balance problems tend to arise. In addition, there are instances when surgical fluids such as blood plasma or whole blood in an emergency situation are literally pushed into a patient. That is, the bag connected to the patient through an I.V. line is squeezed very hard to force in as much fluid in as short a time as possible. It then becomes difficult to assess the actual amount of fluid, in that the fluid is being rapidly advanced, and the residuals in the bag do not collect in a gravity environment so that the remainder in the bag can be measured easily by eye.

Under such circumstances, it is easy to see how one may lose track of several units of fluid, for there are more immediate tasks at hand than to write down how much blood was used. When the attention of personnel is concentrated on the most important procedure—i.e., cardiac resuscitation—this activity delays the logging of the fluid input until the crisis has passed. Thus under high stress situations, one may forget to log fluids, and this may not only adversely affect the mitigation of the emergency itself but also the short term survival of the patient as it may relate to the circulatory and vascular system.

The need to be advised as to the body fluid balance (the ratio of total fluid input to total fluid output) is by no means confined to surgical procedures. In post-operative care, whether in a critical care unit or in an intensive care facility, the patient is usually treated intravenously with various medications. Also, means may be provided to continue to draw exudate from the surgical site.

It is essential that the status of medications and their effect on the patient be exactly known, for medicaments not only influence metabolism but also affect post-operative recuperation time and post-operative well being. During the post-operative period, it is vital that careful control be maintained over the input of medicaments; for an excessive amount of certain drugs may have a fatal effect, whereas an insufficiency of others may lead to organ necrosis, cardiac failure, or other terminal disorders.

Even in those procedures where no surgical procedures have been performed on a patient, such as a patient entering a hospital with cardiac arrest, his fluid balance must be very tightly controlled because of the nature of his medical complaint. Under such circumstances, medication may be given to the patient which increases the amount of urine excreted from his body, thus depleting his body of fluid. (The patient probably is under general anesthesia for pain or to induce sleep and cannot advise the medical staff when he needs more fluid to replenish that which his body has cycled.) Therefore, the fluid balance of this patient is critical. With cardiac and pulmonary patients, the body fluid level and the electrolyte balance are critical for basic survival. The concern of this invention is, therefore, not limited to surgical procedures or post-operative care, for it embraces patients who have never had a surgical procedure but have been admitted to the hospital for a variety of other complaints. Among the complaints to which the invention is appropriate are cardiac patients, diabetics, pneumonia patients, patients suffering from pulmonary edema or other pulmonary disfunctions.

Present control procedures for this purpose depend largely on the ability of the attending nurse to carefully check from time to time the various fluid input and output sources and to report any irregularity to the physician in charge. These control procedures are, of course, subject to human error and negligence. The level of work pressure in a crical care unit or cardiac care unit, even in the smaller hospitals, is high. Hospitals are having to treat an increasing number of people on an extreme situation basis, and the facilities of most hospitals have not kept up with the volume. In a case where a critical care unit has ten beds and only three or four nurses to staff those beds, should an emergency occur in one or two of those beds, all attention is diverted to terminating the emergency, the condition of the other patients being ignored for as long as it takes to correct the problem. In some cases, this neglect has been fatal to patients not involved in the emergency.

Not only in terms of work pressure is the problem substantial but also in regard to the complexity and the range of drugs and medication that can be dispensed to a patient. It is easy to miscalculate a dosage for a patient when one has to recalculate the dosage each time the particular drug or medication is administered because of changes in fluid level of the patient. Even with the best of nursing care, there are circumstances when the instantaneous nursing peak work load is too great, and significant or critical parameters of either the patient under immediate concern or other patients in the critical care ward are brushed aside because of lack of staff. Yet the rate at which certain substances are infused and the total amount of the substances given to a patient may make the difference between success or failure.

SUMMARY OF INVENTION

In view of the foregoing, the main object of this invention is to provide a medical-electronic body fluid accounting system for use in surgical procedures, post-operative care, and general patient care where indicated, to afford a running account of the fluid intake to a patient and the fluid losses therefrom, the account being in a form which is recordable.

More particularly, an object of this invention is to provide a system of the above type which includes a computer to which is fed digital data representing each fluid input and each fluid output source, the computer digesting this data to yield a fluid input total and a fluid output total making it possible for supervisory personnel to have a running account of the patient's fluid input-output balance, as well as a temporal history recorded of the fluids dispensed and removed.

Yet another object of this invention is to provide a computerized fluid accounting system which obviates the need for physicians, nurses, or other personnel to maintain a constant watch on fluid intake and output, yet minimizes the possibility of an unacceptable imbalance arising between fluid intake and output.

Still another object of the invention is to provide a system whereby analysis not only of urine but also blood and other outputs from the patient as well as a real time control analysis of all of the inputs of the patient can be carried out using one primary piece of computer equipment and many peripheral devices, all of the information derived by the peripheral devices being brought to one central point for analysis, accounting and display. After this information has been analyzed, the computer, based on programmed criteria, can make decisions and alter fluid inputs, or in some cases outputs, in order to control or stabilize and maintain a specific level of fluid or medication in the patient's body.

A significant feature of a system in accordance with the invention is that the computer, by storing nominal data regarding prescribed fluid values and comparing the stored data with the running values can signal an alarm when an unacceptable deviation is sensed. Also, the computer is capable of acting as a process controller which in response to a deviation in fluid input from the prescribed value serves to regulate the fluid input to conform it to the nominal value.

Also an object of the invention is to provide an efficient, reliable and compact accounting system of the above type which can be manufactured at relatively low cost.

Briefly stated, these objects are attained in a medical-electronic body fluid accounting system for use in surgical procedures, and in post-operative and non-surgical care to afford a running account of the fluid intake to a patient and fluid losses therefrom. The system is provided with a microcomputer to which is applied digital data derived from a plurality of fluid input source and fluid output source channels which together represent all of the prevailing fluid input and output sources associated with the patient. Included in the input source channels are those monitoring the flow of fluids being fed intravenously into the patient, each such input channel having a sensor which generates a signal representing the volume of a particular fluid, such as a saline solution, being infused into the patient, this signal being converted into a corresponding digital value. The computer is provided with a keyboard to allow manual entry of fluid inputs in those situations where flowmeters for fluid measurement are not possible. Thus if a certain amount of a drug is injected into a patient on a one-shot basis, this amount may be entered into the computer by way of the keyboard, the computer logging this entry and the time thereof.

Included in the output source channels is a sensor generating a signal representing the amount of fluid discharged through a urinary or other catheter, a sensor generating a signal representing the amount of exudate drawn from the surgical site, another to measure fluid taken from the patient via a Levine (N.G.) tube, and still another with a sensor to measure the amount of blood taken from the patient by sponges.

In respect to output fluids, the keyboard associated with the computer may be used to enter material removed from the patient which is heavily laden with fluid and which cannot be automatically measured by any specific output data acquisition channel. The nurse or surgeon would then simply key in the amount of fluid as weighed on a scale or otherwise derived, and also key in the nature of the fluid removed from the patient. The computer would then log and account for the keyed-in output data, and also log in the time of the entry.

On the basis of data acquired by the input and output channels, the computer yields a fluid input total and a fluid output total, which totals are displayed to indicate the prevailing fluid balance. Integrated into the accounting system are additional sensors which in conjunction with the computer carry out urine analysis and perform other analytical functions in real time, such as specific blood analysis, which analyses reflect the level of medication in the patient's body.

A system in accordance with the invention significantly reduces the margin of error in critical care, intensive care units, cardiac units and wards; for in such units the nurses who are responsible for several patients do not have the time to stand over each patient and monitor on a continuous basis the medications being delivered intravenously to the patient. Because metabolic rate varies from patient to patient and surgery affects patients in different ways, there are not absolute criteria for setting IV's, but only an empirical approach that is subject to frequent adjustment by the nursing staff. Because the present method of setting IV's is imprecise and gives only a fast approximation, for most patients the amount of input fluid is not well controlled unless an IVAC type system is used. With a system in accordance with the invention, one may program into the computer the medications being dispensed and monitored, the program establishing the levels of medication prescribed for the patient. The information yielded by the computer is read and compared against a reference table that is entered in computer memory on an individual patient basis, corrections being made in the input side of the system in response to data derived from what is excreted or drained from the patient.

OUTLINE OF DRAWINGS

Figure 2:
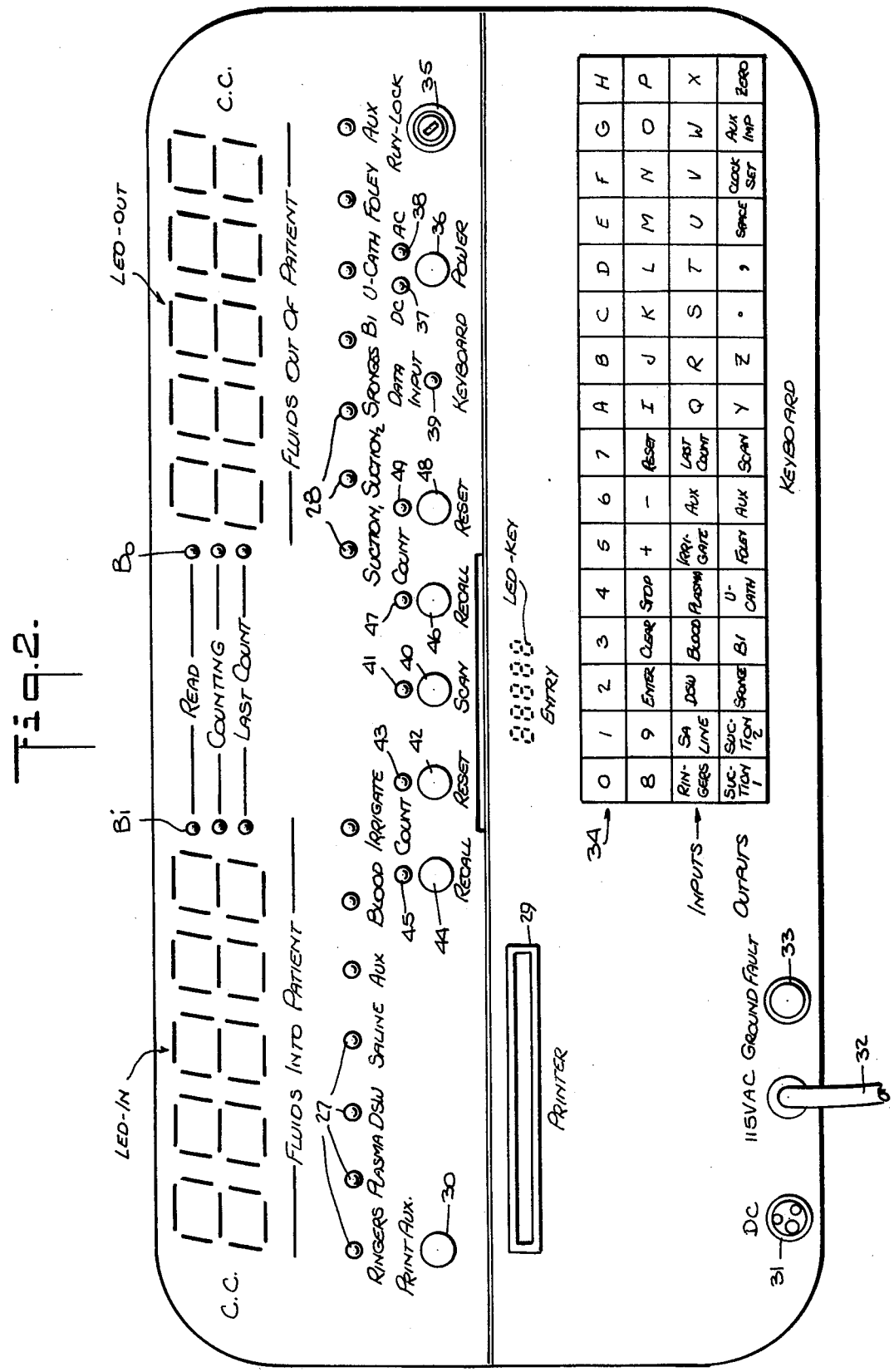

For a better understanding of the invention as well as other objects and further features thereof, reference is made to the following detailed description to be read in conjunction with the accompanying drawings, wherein:

FIG. 1 is a block diagram of a fluid body medical-electronic accounting system in accordance with the invention; and FIG. 2 shows the control and display panel of the system.

DESCRIPTION OF INVENTION

The Basic System

Referring now to FIG. 1, there is shown the basic elements of a medical electronic accounting system in accordance with the invention, the system including channels A to G which supply data in digital form to a digital computer which acts to digest this data to yield information regarding the total fluid input to a patient and the total fluid output. Because of the bus-oriented architecture of the system, as many as a thousand inputs and outputs can be connected to the communication line, channels A to G being merely representative thereof. It is to be understood, therefore, that the invention is such that virtually any number of uniquely addressable, analytical instruments may be attached to the communication bus, particularly since the computer operates far more rapidly than what is taking place in the human body.

A digital computer is capable of carrying out arithmetic or logic operations on data entered therein and of yielding numerical results or decisions. Whether in the form of large-scale, general-purpose computer, a mini-computer or a microcomputer, all digital computers are essentially composed of a central processing unit represented in FIG. 1 by microprocessor 10, a memory system and some form of an input-output device.

The task assigned to a central processing unit 10 is to receive and to store for later processing in a memory 11 data in the form of binary digits or bits, to perform arithmetic or logic operations on this data in accordance with previously-stored instructions, and to deliver the results through a read-out device such as a printer 12 or a cathode ray display terminal 13.

The central processing unit is that component of the computer which controls the interpretation and execution of instructions. In general, a CPU contains the following elements: "Control" which includes control logic and instructions for decoding and executing the program stored in "Memory;" "Registers" which provide control with temporary storage for bits, bytes or words; and Arithmetic and Logic Unit that performs arithmetic and logic operations under the supervision of Control; and Input-Output ports providing access to peripheral devices such as keyboard 14 and cathode ray terminal 13.

The memory system is that component of the computer which holds data and instruction codes, each instruction or datum being assigned a unique address that is used by the CPU when fetching or storing the information. The read-only memory or ROM is a memory adapted to store information permanently, such as a math function or a micro-program (a special purpose program initiated by a single instruction in the system's main program.) A memory that can be programmed by the user, but only once, is known as a programmable ROM or PROM; hence when a PROM is programmed, it then functions as a ROM. Included in the computer is a PROM 15.

The capability of a computer depends in good part on the storage capacity of its memory system. The amount of information stored ranges from fewer than 100 bits, as in a simple pocket calculator, to more than a billion bits for a large-scale computer. Integrated-circuit memories based on transistors are designed to store bits of binary digits on a chip.

The basic "hardware" components of a digital computer are the central processing unit (CPU), the memory system and input-output devices. The registers, the control and the arithmetic logic unit of the CPU are linked with the memory system and the input-output device by a data bus; that is, a group of wires that allows the memory, the CPU and the input-output device to exchange signal bits, bytes or words. Also associated with microprocessor 10 is a real time clock 16. The computer is energized by a power supply 17 having a battery pack back-up 18 so that the power remains uninterrupted should the supply fail. Memory 11 includes a local lithium battery so that the memory is non-volatile and will continue to store data in the event of a power failure.

The computer is associated through bus 19 with channels A through G, each channel supplying to the computer digital data derived from a sensor which detects a particular activity germane to the patient's condition. Thus sensor $S_a$ in channel A takes the form of a sponge-weighing platform which provides an analog signal proportional to the weight of a surgical sponge saturated with blood and other body fluids removed from the patient on the surgical table. The function of channel A is to supply the computer with data regarding the amount of blood and other fluids extracted by sponges from the patient.

Because of the bus-oriented architecture of the computer, it is possible to attach virtually an unlimited number of discrete devices to the computer as long as the formal organization of the communications data is the same as that read by the computer. In addition, one may attach other devices to the computer which have the same data format, as well as having the computer communicate bidirectionally with such devices (assuming such devices have bidirectional communications capability).

The output signal from sensor $S_a$ is applied to a signal conditioner $C_a$ which may include an amplifier whose output is fed to an analog-to-digital converter A/D to provide a corresponding digital value. This value is held in a latch circuit $L_a$. Microprocessor 10 cyclically samples the channel outputs in sequence; hence when the digital value from latch $L_a$ is delivered to the microprocessor, the latch is then reset to receive the next digital value regarding sponged fluids.

The computer may also be programmed to poll all of the input and output devices on the communication line, or to only respond to devices on the communications line which have updated their data. In this manner when a high density of devices are used (thirty or forty), the computer will not waste timing polling information points where the data has not changed. In other words, the computer will not poll devices that carry the same information that they had in the last transaction. In this way, the computer can increase its efficiency and increase its speed of acquiring data.

In order to know the exact weight of the blood and other fluids picked up by the saturated sponge, one must subtract therefrom the tare weight of the unsaturated sponge. Since standard lap sponges are used in surgical procedures having known tare weights, the tare weight thereof is stored in computer memory; and when data is received from channel A, the computer then acts to subtract the tare weight from the gross weight of the blood-saturated sponge to provide the exact weight of the fluid taken out of the patient by the sponge.

Sensor $S_b$ in channel B acts to determine the amount of exudate withdrawn from the patient by a suction pump coupled by a suction line to the surgical site. For this purpose, sensor $S_b$ may take the form of a weighing platform on which is placed a container receiving the discharge from the pump. Or this sensor may take the form of a mass flowmeter interposed in the suction line of the pump. The signal from sensor $S_b$ is processed by signal conditioner $C_b$ and converter $A/D_b$ to provide digital data representing the exudate.

In a typical surgical procedure, the exudate may be a mixture of blood, saline solution or any irrigate used by the surgeon in the course of the procedure. When it is necessary to know the ratio of blood to the other fluids constituting the exudate, the suction line may have a red blood cell counter interposed therein, which functions as a blood sensor. In this instance, a separate channel (not shown) is provided for the blood cell sensor to provide digital data regarding the volume of blood extracted by the pump. In this way, the fluid total in the computer can be corrected for the actual running total of blood removed from the patient by suction, as distinguished from the amount removed by sponges.

Channel C acts to determine the amount of fluid withdrawn from the patient by a particular catheter. In surgical procedures, in addition to a urinary catheter, use may also be made of a Foley catheter for excretions, a gastrointestinal catheter, and others. There will be a separate channel for each catheter or drain channel C representing only one of these catheter channels.

In practice, there may be associated with each catheter a blood cell counter and/or a sugar sensor or other analytic instrument, each providing data to a respective channel dedicated thereto. The blood cell counter will therefore advise the computer, in the case of a urinary catheter how much actual blood is coming out of the patient through the urinary tract as opposed to other fluids. And the sugar counter channel will run a simple sugar presence test to tell the computer the amount of urine sugar or acetone being execreted, or the specific gravity of the excrement. This information is especially useful in the case of a diabetic patient subject to post operative and chemical complications.

The computer may be programmed to set off an alarm 20 when, for instance, the sensed sugar level crosses predetermined upper or lower limits. Also, the computer can function, in a manner to be later explained in greater detail, to command a controller operating a valve or other control element to regulate the flow of a medicant should the sugar level rise above or fall below preset limits.

In addition to sensing sugar, since the computer is capable of communication with any digital data, other medication levels, blood gas, pH, calcium levels, potassium levels, urine acid, urine protein, urine blood, etc. can be evaluated. These then can be used, with proper programming, by the computer to generate information which when acted on by the computer program will generate a result used to control medication inputs or other inputs to the patient based on the analyzed data.

Channel D includes a sensor $S_d$ interposed in a venous line (or an IV line) to take a blood sample at programmed intervals and to analyze the blood flowing through the line for specific medicants or other parameters to provide a signal indicative thereof. Channel D is not concerned with the amount of fluid input or fluid output and does not, therefore, play a role in a determination of the total fluid input or output. However, since the fluid input-fluid output accounting system makes use of a computer capable of carrying out much more than accounting functions, the computer is exploited for other purposes, such as to determine the degree to which the patient's blood shows traces of a medicant being administered to him.

Keyboard 14 is used to enter limits with respect to the medications prescribed for the patient to which the system must be alerted. The computer, acting on data derived from the medication analysis performed by sensor $S_d$, makes a decision after going through its algorithmic processing, and sends commands to the appropriate IV controllers to adjust the flow of the appropriate IV controllers to adjust the flow of the appropriate medication so that the medication sensed in the venous blood line is at the preprogrammed level. If, for example, one of the IV lines carries lactose and the venous blood is deficient in lactose-related metabolites, the supply of lactose will then be increased to attain the desired level.

In some instances, the lap sponges used by a surgeon are dampened before being used at the surgical site. The liquid which dampens the sponge represents a liquid input to the patient. Hence in channel E, sensor $S_e$ acts to meter the amount of dampening fluid added to the sponge so that the digital data entered into the computer by this channel can be used to subtract the measured amount of sponge dampening fluid from the total fluid count.

Channel F includes a sensor $S_f$ whose signal depends on the amount of fluid flowing through a given IV line feeding the patient. In practice, sensor $S_f$ may take the form of a drip counter interposed in the IV line or some form of conventional flowmeter. Thus, after this signal is converted into a digital value in $A/D_f$ and latched in latch $L_f$, it is supplied to microprocessor 10, for this value represents a fluid input to the patient. In practice, there is a channel associated with every one of the several IV lines used in the procedure.

The microprocessor, since it receives data as to each of the several IV fluid inputs, may be programmed to function as a closed loop control system to maintain the flow rate in each IV line at a programmed value. To this end, each IV channel such as channel F is associated with a valve V interposed in the IV line, the valve being governed by a suitable controller Con (as in an industrial process control system) which receives an error signal from the computer that depends on the deviation of the IV flow rate from a prescribed set point stored in the computer.

This error signal is fed to a digital-to-analog converter D/A. The analog output of converter D/A is applied to controller Con which operates valve V in a direction to an extent causing the IV flow therethrough to assume a desired rate. Thus valve V acts effectively as the final control element in a process control system. In a relatively simple embodiment of the system, the computer will operate with a maximum of thirty-two inputs and thirty outputs. But the system lends itself to expansion, and there is no reason why the bus communication density cannot have up to a thousand inputs and a thousand outputs, limited only by the memory capacity of the microcomputer.

In addition, by appropriate programming in the computer, a valve controller Con can be used to adjust medication levels in the blood by operating on data given to the controller by the microprocessor that has been analyzed by a venous line sensor, arterial or urine sensor.

Channel G represents a single channel or set of channels that allows external sensors $S_g$ having either analog or digital outputs fed to an analyzer AN to be plugged into the system. A personality module adapter PM is interposed in channel G so that the communication organization, bit structure, parity and voltage level can be adjusted whereby adequate high speed communication can be had with adequate buffering and isolation.

Fluid input display 21, which may be an LCD or LED multi-station digital display, is coupled to microprocessor 10 through a suitable driver 22, the display giving the total input of fluids delivered to the patient in the course of the surgical procedure or during postoperative care. Fluid output display 23 is coupled to the microprocessor through driver 24 to provide a reading of the total fluid output drawn from the patient by catheters, by a suction pump and by sponges. Thus the observer sees on the control panel, as shown in FIG. 2, a side-by-side reading of the total fluid fed into the patient and the total fluid taken out of the patient.

This system is designed for an "on patient" kind of monitoring, to be attached to the side of the bed, Gurney, wheelchair or other mobile equipment or nonmobile piece of equipment such as an operating table. The displays have been specifically designed in order to facilitate the rapid nonconfusing interpretation of data by physicians, anesthesiologists, surgeons, and nurses.

It should be appreciated, however, that for fully integrated, multiple sample display of data a cathode ray tube display 13 would be used. This CRT display would be associated with a central station which monitors a number of patients at the same time through similar hardware connected to the same central computer.

The control panel may be programmed to scan through all of the different connected channels of input and output sensors or give displays of only running totals without regard to the source from whence they came, or to give displays or past readouts of single sources on command. The buttons illustrated in the drawing execute those functions as called up by the physician, nurse, anesthesiologist, or surgeon. In addition, the machine can be called to run a preprogrammed format (in other words, scan through all of the levels in a preprogrammed order so that a sequence of digits flashing on each display represents an amount of fluid withdrawn or put into the patient which corresponds to the identified channel).

In addition to input and output monitoring, accounting and evaluation of information, the input lines of the device as well as the output lines may be equipped with a rate sensor in order to measure as well as control the rate at which a medication is given rather than simply the total volume. It is necessary under certain circumstances to provide a low initial dose of some drug to a patient and slowly increasing the dose to a substantially higher level. Conversely, it may be necessary with some medications to start with a very large dose and slowly over a protracted period of time decrease the dosage substantially. The computer may be designed to not only monitor but to control these functions as well as to enter the varying inputs and outputs into the fluid accounting.

Also associated with the computer is an input source display 25, so that when the appropriate button is pressed on the control panel, such as a button for Ringer's lactate, the fluid input display 21 will then switch over to an indication of the amount of lactate delivered to the patient. Pressing another button will give an indication of the blood plasma delivered, and so on, with respect to the buttons on the input side. The buttons on the output side for output source display 26 include a button which, when pressed, will switch the fluid output display to the amount of exudate extracted by the suction pump. Pressing another button will provide an indication of the amount of fluid extracted through the urinary catheter, and so on with respect to the other buttons on the output side.

All information yielded by the system may be recorded on the printer 12 which provides a running record of the patient's treatment. The printer is preferably in moving chart form, with the significant data printed along a time scale so that a hard, real-time copy is made available for future review and analysis.

Control and Display Panel

Referring now to FIG. 2, there is shown one embodiment of a control and display panel usable in a body fluid accounting system in accordance with the invention. The upper portion of the panel is effectively divided into an input fluid section and an output fluid section. The input section is provided with an LED digital display designated LED-in composed of five stations, each having a seven-segment LED unit capable, by selective actuation, of presenting the numerals 0 to 9. The output section is provided with like LED digital display designated LED-out. These displays give a reading of total fluid input and total output in C.C. terms.

Interposed on the panel are two sets of status indicators $B_i$ and $B_o$ in the form of pilot lights which function to independently indicate what the digital input and output displays are presenting at a particular moment; that is, whether the input or output display is operating to "READ," for "COUNTING" or presenting the "LAST COUNT."

To identify the fluid or fluids being fed into the patient, placed below the LED-in display is a row of pilot light or LED indicators 27 to identify such input fluid sources as Ringers, Plasma, D5W, Saline, Aux, Blood, Irrigate. These sources are given by way of example only.

To identify the fluids being taken out of the patient, placed below the LED-out display is a row of pilot lights or LED indicators 28, the first two being for SUCTION sources; the next for SPONGES; then one for BI; one for a urinary catheter; one for a FOLEY catheter, and one for an AUXILIARY output source. Here again, these fluid outtake sources are by way of example only.

In practice, the fluid source indicators may be of the two color type, so that when the light turns green, this indicates that a peripheral monitoring device is connected to the patient and is being read and displayed by the system; whereas when the light turns red, this means either that the peripheral monitoring device for a particular source is connected but is on standby and is therefore not being read or displayed. If there is no light, it means that this device is not connected.

A printer slot 29 is provided from which emerges a chart or printed paper record of all transactions. Operation of button 30 causes the chart paper to advance out of slot 29 so that it can be torn off.

Below printer slot 29 on the panel is a d-c socket 31 into which one may plug a cable coupling the system to a back-up battery pack. A cable 22 passing into the panel supplies A-C power thereto, device 33 adjacent this cable being a ground fault interrupter circuit breaker.

The lower portion of the panel is largely given over to a manually-operated keyboard 34 which includes key pads for entering digits 0 to 9, key pads for entering letters A to Z and punctuation marks. Also included are a row of dedicated keys to enter fluid inputs, such as Ringers, Saline and Blood, and a row of dedicated keys to enter fluid outputs such as Suction 1, Sponge and Urine Catheter. These keys are operated when there is no automatic monitoring channel to meter the fluid in question, and manual entry is then necessary to account for the fluid. The keyboard shown is intended only to represent one form of a suitable manual entry arrangement.

It is to be understood that the keyboard shown functions to provide entries related to a given patient, this keyboard being directly accessible to those attending the patient. Where the same computer is shared by a large number of patients, a central computer will then have a full standard keyboard by which entries can be made that are not personal to a given patient but are appropriate to all of the patients under computer supervision and control.

In its simplest form, the system may be designed as a bedside accessory to carry out accounting for a single patient, in which case the device may be highly compact, with the control and display panel acting as a mini-station operating in conjunction with a microprocessor to analyze the automatically monitored fluid inputs and outputs as well as those manually entered on the keyboard.

Also provided on the control panel is a "Lock" switch 35 which when operated freezes the display or permits the system to work "Run." The purpose of this key lock switch is to save data in the case of a necessary interruption so that displays will not then be lost. The power switch 36, which may be in push-button form, turns the system "on" or "off," the "on" and "off" status (battery or AC) being indicated by LED pilot lights 37 and 38. An LED pilot light 39 flashes when keyboard data is being entered.

The miniature five station LED display designated "LED-key" acts to present keyboard entry data for confirmation before the data is admitted to the microprocessor for computation. In practice, this display may, when the keyboard is quiescent, be used to provide a timekeeping display.

The "Scan" button 40, when actuated, puts the system in the scan mode, in which mode the fluid input and output displays LED-in and LED-out, are caused to step sequentially from fluid monitoring channel to channel to provide successive readings of individual fluid values. In this way, the LED displays not only afford a total fluid input and a total fluid output reading so that the observer can see the overall balance therebetween; but the observer can, by pressing the scan button, also see what each monitoring channel is doing. A pilot LED 41 above the scan switch 40, when "on" indicates that the display is in the scan mode.

On the fluid input side, a "reset" switch 42, when actuated, as indicated by pilot light 43, resets the display to "00000." When "recall" switch 44 is actuated, as indicated by pilot light 45, the last number counted is recalled as the source is identified. On the fluid output side, like functions are performed by "recall" switch 46 and its indicator 47, and "reset" switch 48 and its indicator 49.

When the display takes the form of a cathode ray terminal, then the terminal is provided with a keyboard generally of the type shown in FIG. 2, and the readout and other functions, which in FIG. 2 are carried by LED's and other indicators, are presented on the screen of the cathode ray tube.

While there has been shown and described a preferred embodiment of a medical-electronic body fluid accounting system in accordance with the invention, it will be appreciated, however, they may changes made be made therein without departing from the essential spirit thereof.

We claim:

1. A body fluid medical-electronic accounting system for use in surgical procedures to afford a running account of fluid balance constituted by the ratio of the total fluid intake to a patient to the total fluid outtake therefrom, said system comprising:
   A. a digital computer;
   B. a plurality of data channels coupled to the computer related to the prevailing fluid input and output sources associated with the patient in the course of a given surgical procedure, each data channel including a sensor to sense a respective fluid to produce an analog signal as a function thereof, one of said output source channels having its sensor coupled to means for measuring the amount of blood and other fluids extracted from the patient by a sponge in the course of said surgical procedure, and means to convert the signal from each of the sensors in the system into a corresponding digital value to be entered into the computer, the computer digesting the data acquired by the respective channels and performing computations to yield a fluid input total and a fluid output total; and C. display means coupled to the computer to indicate said input and output totals to provide a reading of the fluid balance.

2. A system as set forth in claim 1, wherein said fluid input source channels are coupled to lines feeding medicants intravenously into the patient.

3. A system as set forth in claim 2, wherein each of said fluid input source channels include a sensor in the form of a drop rate detector interposed in the line.

4. A system as set forth in claim 1, wherein one of said output source channels has its sensor coupled to a urinary catheter.

5. A system as set forth in claim 1, wherein one of said output source channel has its sensor coupled to a catheter through which flows a fluid discharged from the patient.

6. A system as set forth in claim 1, wherein said means to indicate said input and output totals is constituted by respective digital display stations.

7. A system as set forth in claim 1, wherein said means to indicate said input and output totals is constituted by a cathode ray tube terminal.

8. A system as set forth in claim 1, further including a printer coupled to said computer to record said totals.

9. A system as set forth in claim 2, wherein said medicant lines include a valve to adjust the flow therethrough, and said computer is programmed with respect to each medicant to operate a controller for regulating the valve to maintain a desired flow rate.

10. A system as set forth in claim 2, further including alarm means associated with the computer to indicate an acceptable level of medicant in the blood or vein of the patient.

11. A system as set forth in claim 1, further including a keyboard associated with said computer by which data is entered relating to fluid inputs and outputs which is not sensed by said channels.

12. A system as set forth in claim 11, wherein said keyboard includes keys dedicated to identified fluids.

13. A system as set forth in claim 12, wherein said keyboard includes alpha-numeric keys.

14. A system as set forth in claim 1, further including means to operate said display means in a scan mode in which the data produced by the respective channels is sequentially presented.

15. A system as set forth in claim 1, wherein the means which measures the amount of blood and other fluids extracted from the patient is constituted by a sponge-weighing platform which provides an analog signal proportional to the weight of the sponge saturated with the blood and other body fluids.

16. A system as set forth in claim 15, wherein the tare weight of the sponge in its unsaturated state is stored in the memory of the computer, which tare weight is subtracted from the gross weight of the saturated sponge to provide the exact weight of the fluids taken out of the patient by the sponge.

* * * * *